US010052456B1

(12) United States Patent
Chiu et al.

(10) Patent No.: US 10,052,456 B1
(45) Date of Patent: Aug. 21, 2018

(54) FLEXIBLE CATHETER

(71) Applicant: SEISA Soparfi S.A.R.L., Luxembourg (LU)

(72) Inventors: Aaron Chiu, El Paso, TX (US); Enrique Delgado Macias, Chihuaha (MX)

(73) Assignee: SEISA Soparfi S.A.R.L., Luxembourg (LU)

( * ) Notice: Subject to any disclaimer, the term of this patent is extended or adjusted under 35 U.S.C. 154(b) by 0 days.

(21) Appl. No.: 14/815,822

(22) Filed: Jul. 31, 2015

Related U.S. Application Data

(60) Provisional application No. 62/032,504, filed on Aug. 1, 2014.

(51) Int. Cl.

| A61M 31/00 | (2006.01) |
|---|---|
| A61M 25/00 | (2006.01) |
| A61M 25/01 | (2006.01) |
| A61M 25/09 | (2006.01) |
| A61M 39/12 | (2006.01) |
| A61M 39/10 | (2006.01) |

(52) U.S. Cl.
CPC ...... *A61M 25/0045* (2013.01); *A61M 25/005* (2013.01); *A61M 25/0041* (2013.01); *A61M 25/0054* (2013.01); *A61M 25/0113* (2013.01); *A61M 25/09041* (2013.01); *A61M 39/10* (2013.01); *A61M 39/12* (2013.01); *A61M 2025/0047* (2013.01); *A61M 2025/0062* (2013.01); *A61M 2205/0216* (2013.01); *A61M 2205/0238* (2013.01); *A61M 2205/0266* (2013.01); *A61M 2210/083* (2013.01); *A61M 2210/125* (2013.01)

(58) Field of Classification Search
CPC ........ A61M 25/0041; A61M 2039/062; A61M 25/104; A61M 25/0045; A61M 25/005
USPC ................................ 604/510, 280, 281, 523
See application file for complete search history.

(56) References Cited

U.S. PATENT DOCUMENTS

| 5,401,258 | A | 3/1995 | Voda | |
|---|---|---|---|---|
| 5,439,445 | A | 8/1995 | Kontos | |
| 5,876,385 | A * | 3/1999 | Ikari | A61M 25/0041 604/523 |
| 6,645,160 | B1 | 11/2003 | Heesch | |
| 8,246,574 | B2 | 8/2012 | Jacobs et al. | |

FOREIGN PATENT DOCUMENTS

| EP | 0829270 B1 | 3/1998 | |
|---|---|---|---|
| WO | WO 2012130878 A1 * | 10/2012 | ........ A61M 25/0041 |

* cited by examiner

*Primary Examiner* — Phillip Gray
(74) *Attorney, Agent, or Firm* — Carr Law Firm PLLC

(57) ABSTRACT

The present invention provides a flexible catheter system and method for providing easier access and delivery of therapeutics and or devices via the human vasculature. The flexible catheter system comprises a luer connector attached to a flexible catheter body by a proximal shaft. The method includes the steps of providing a patient in need of an interventional procedure, obtaining a flexible catheter system, inserting the flexible catheter system into the patient through the right radial artery located in the right arm of the patient, and tracking the flexible catheter body from the right radial artery to the heart of the patient.

32 Claims, 4 Drawing Sheets

FLEXIBLE CATHETER

CROSS-REFERENCE TO RELATED APPLICATIONS

This application relates to, and claims the benefit of the filing date of, U.S. provisional patent application Ser. No. 62/032,504 entitled "FLEXIBLE CATHETER", filed Aug. 1, 2014, the entire contents of which are incorporated herein by reference for all purposes.

BACKGROUND OF THE INVENTION

Field of the Invention

The present invention relates to catheters and, more particularly, to a flexible catheter system with a flexible catheter body having a particular shape.

Description of Related Art

Cardiac catheterization is a method doctors use to perform many tests and procedures available for diagnosing and treating coronary artery disease. The method involves threading a long, thin tube (called a catheter) through an artery or vein in the leg or arm and into the heart. Depending on what the doctor wants done, different things may happen during cardiac catheterization. For example, one may have angioplasty, which uses a balloon on the end of the catheter to open narrowed arteries in the heart. One may also have a stent, a small, mesh-like device made of metal that acts as a support, or scaffold, inside of a vessel, placed at the time of angioplasty.

During these procedures, doctors usually gain access to the arteries of the heart by placing the catheter in the femoral artery and threading it up and into the heart. The femoral artery is a major artery in one's groin area. Even though this is the most popular method, femoral artery access can cause many problems, such as bleeding at the puncture site and nerve damage. Also, after the procedure, patients need to lie very still for at least five hours to make sure that the puncture site in the femoral artery does not start to bleed again.

But the femoral artery is not the only route that can be used to reach the heart. Doctors can also use the radial artery, which is an artery in one's wrist. Because the radial artery in the wrist is smaller than the femoral artery in the groin, it much easier to apply direct pressure to the puncture site to stop the bleeding. For most patients, radial access does not cause as much discomfort as femoral access does. Also, radial artery access allows many patients to get out of bed and walk around right after their procedure.

Interventional cardiologists performing a procedure through radial artery access will generally use the radial artery in the wrist as the entry point for the catheter. The cardiologist threads the thin catheter through the body's network of arteries in the arm and into the chest, eventually reaching the heart. This process may also be referred to as transradial access, the transradial approach, or transradial angioplasty. The present invention is a flexible catheter system that utilizes the transradial approach.

SUMMARY OF THE INVENTION

The present invention includes a flexible shaped catheter system and method that provides easier access and delivery of therapeutics and or devices via the human vasculature. In one embodiment of the present invention, the flexible catheter system includes a luer connector and a flexible catheter body. The flexible catheter system may be introduced into the patient vasculature via the arm so as to access and accomplish easy introduction into the vasculature.

BRIEF DESCRIPTION OF THE DRAWINGS

For a more complete understanding of the present invention and the advantages thereof, reference is now made to the following Detailed Description taken in conjunction with the accompanying drawings and in which.

DETAILED DESCRIPTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Figure 1:
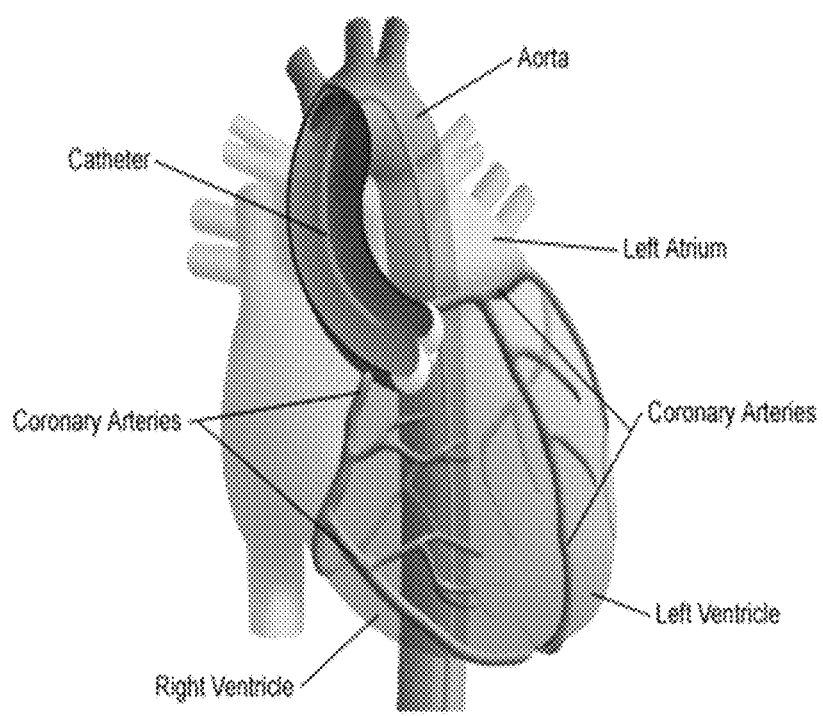
FIG. 1 depicts an intravascular procedure using the prior art catheter.

FIG. 1 depicts an intravascular procedure using a prior art catheter. Traditional approaches to gaining access to the arteries of the heart require placing the catheter in the femoral artery and threading it up and into the heart. The femoral artery is a major artery in one's groin area. After being threaded through the femoral artery, the catheter enters the aorta as shown in FIG. 1 to reach the heart.

Figure 2A:
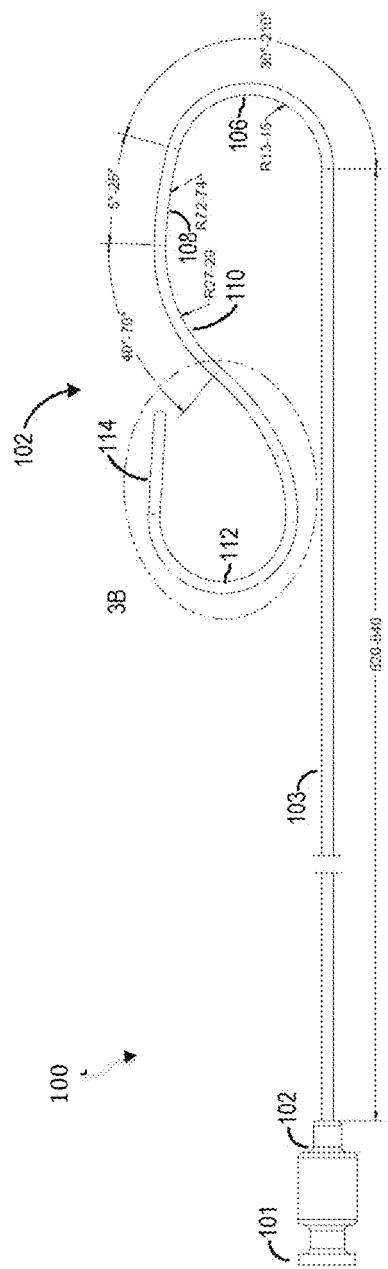
FIGS. 2A-2B depict a lateral view of one embodiment of the flexible catheter system.
Figure 2B:
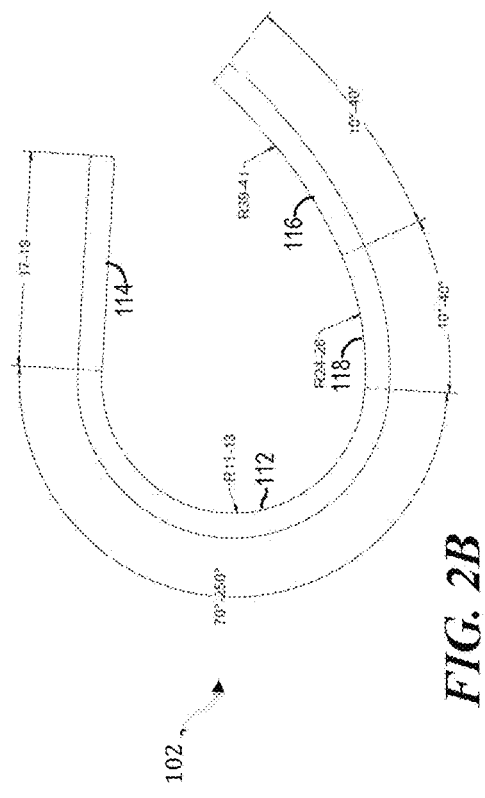

Turning now to FIGS. 2A-2B, one embodiment of the flexible catheter system 100 is shown in a lateral view with a close up of one part of the catheter in FIG. 2B. In FIG. 2A, luer connector 101 is shown connected to proximal segment 103 by a substantially straight proximal shaft 102. The proximal segment 103 can be comprised of a soft to stiff durometer plastic based material, and, in one embodiment as shown in FIG. 2A, have a length in the range of 820-840 mm. Proximal segment 103 then transitions into the distal curved shape 102 which includes first curve 106, followed by a second curve 108, a third curve 110, a fourth curve 112, and distal tip 114.

Curve Description

Focusing now on distal curved shape 102 in FIG. 2A, the first curve 106 adjoining proximal segment 103 may have a curve radius in the range of 13-15 mm and a curve angle in the range of 30°-210°, and may adjoin and transition into the second curve 108. The second curve 108 may have a curve radius in the range of 72-74 mm and a curve angle in the range of 5°-24°, and may adjoin and transition into the third curve 110. The third curve 110 may have a curve radius in the range of 27-29 mm and a curve angle in the range of 40°-70°, and may adjoin and transition into the fourth curve 112. The fourth curve 112 may have a curve radius in the range of 11-13 mm and curve angle in the range of 70°-250°, and may straighten into the distal tip 114.

In another aspect, the distal curved shape 102 may be composed of plastic-based materials having different, soft to stiff, durometers at different portions of the distal curved shape 102. The first curve 106 may be comprised of a relatively stiff durometer plastic-based material. The second curve 108 may be comprised of a less stiff durometer plastic-based material. The third distal curve 110 may be comprised of a relatively soft durometer plastic-based material. The fourth curve 112 may be comprised of a softer durometer plastic-based material. The fourth curve 112 then straighten into the distal tip 114.

Turning now towards FIG. 2B which depicts a close up of part of distal curved shape 102, in another aspect of the flexible catheter system, there may be interposed between third curve 110 and fourth curve 112 an intermediate first curve 116 and an intermediate second curve 118. The intermediate first curve 116 may have a curve radius in the range of 39-41 mm and curve angle in the range of 10°-40°. The intermediate second curve 118 may have a curve radius in the range of 24-26 mm and a curve angle in the range of 10°-40° adjacent the first intermediary curve 116. The intermediate first curve 116 and intermediate second curve 118 may be positioned such that the two intermediate curves 116, 118 are flanked by third curve 110 and fourth curve 112.

Catheter Construction

Figure 3:
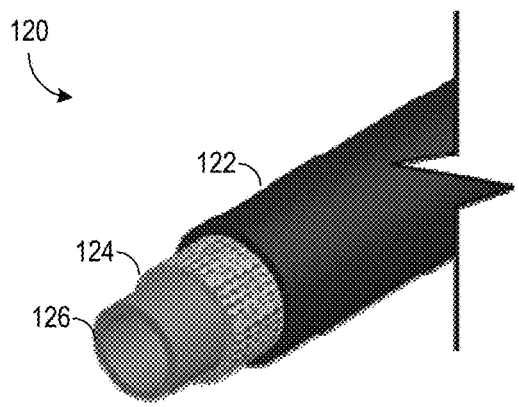
FIG. 3 depicts a cross-sectional view of one embodiment of the flexible catheter system with multi-layer tubing.

Turning now to FIG. 3, a flexible catheter system 120 constructed with multiple layers is shown in a cross sectional view. In another aspect, the flexible catheter system may be composed of several layers of laminate structures. The multi-layer flexible catheter system 120 may have an inner layer 126 with a lubricious path, a middle layer 124 as a reinforcing structure, and an outer layer 122 with shape memory characteristics. The outer layer 122 may be coated with a hydrophilic or hydrophobic material to allow the flexible catheter system 120 or 100 to track with greater ease through the vasculature. The flexible catheter system 100 may lessen coaxial forces which may cause resistance, compression or collapse to the catheter.

Flexible catheter system 120 may be several layers in thickness. Each layer may enable or reinforce the flexible catheter system 120 for better performance and safety when using the flexible catheter system 120. In another aspect, the outer layer 122 may be made of a mix, blend or concentrated plastic-based polyamide, nylon or polyurethane mixed with a radiopaque filler. Examples of radiopaque fillers used in the invention may be different grades and percentages of Barium Sulfate, Tungsten, Bismuth Trioxide, and/or Bismuth Subcarbonate. The radiopaque fillers may allow the flexible catheter 100 to be viewed under X-ray and fluoroscopy procedures in an interventional procedure. The distal tip 114 of the flexible catheter 100 may be comprised of the same radiopaque fillers so that this section may appear "brighter" or easily noticeable under x-ray based procedures such as fluoroscopy.

The outer layer 122 may comprise different segments of durometer along the body of the flexible catheter 100 from its proximal end to the distal tip 114. The outer layers 122 allow for different grades of flexibility. The flexibility of outer layer 122 allows the flexible catheter 100 to maintain its shape. When the flexible catheter 100 is tracked through the vasculature, the "shape memory" lets the flexible catheter 100 engage the coronary ostium using less force due.

The middle layer 124 of the tube 120 may be a braid or coil of wire extending the length of the flexible catheter 120 from its proximal end 102 to the distal tip 114. The second layer 124 may be made from several materials such as different grades of stainless steel, nylon fiber, or nitinol wire, among other materials. The inner layer 126 may include an inner diameter or inner lumen of the tube 120 and may be made of a PTFE Polytetrafluoroethelyne tube or a blend of polytetrafluoroethelyne and plastic-based material so that it is lubricious when in use. The lubricity of inner layer 126 allows for ease of delivery of different devices or therapeutic agents used in interventional procedures. The proximal end of the invention may have a male luer hub 101 for use in conjunction with female luer hubs. The hub may be designed with wings which may enable the user to guide, steer and torque the flexible catheter 100 through the vasculature.

Using the Flexible Catheter

In another embodiment, a method of using a flexible catheter system may comprise: providing a patient in need of an interventional procedure, obtaining a flexible catheter system comprising: a luer connector and a flexible catheter body with a proximal end and a distal end, wherein the flexible catheter body is connected to the luer connector at the proximal end by a proximal shaft, and wherein the flexible catheter body comprises: a proximal segment at the proximal end adjacent to a first curve opposite of the proximal shaft; a second curve adjacent to the first curve opposite of the proximal segment; a third curve adjacent to the second curve opposite of the first curve; a fourth curve adjacent to the third curve opposite of the second curve; and a distal tip adjacent to the fourth curve opposite of the third curve and at the distal end of the flexible catheter body, inserting the flexible catheter system into the patient through the right radial artery located in the right arm of the patient; and tracking the flexible catheter body from the right radial artery to the heart of the patient.

Figure 4A:
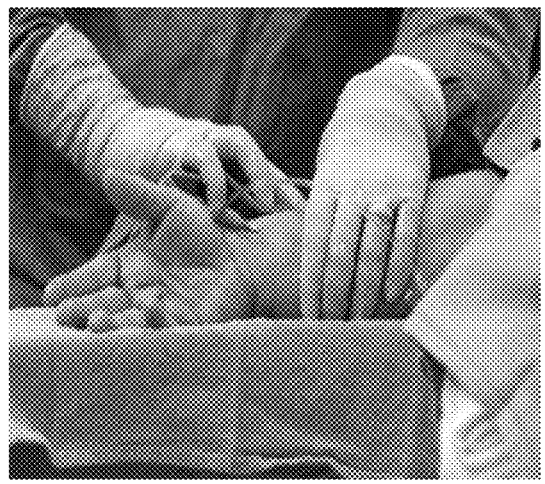
FIGS. 4A-4B depicts the one embodiment of the flexible catheter system being introduced into the body of a patient through the right arm.
Figure 4B:
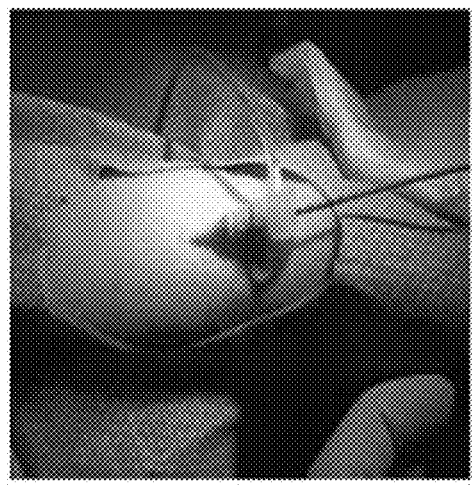

Turning to FIGS. 4A-4B, in another aspect, the flexible catheter 100 may be introduced into the body of a patient via the right radial artery located in the right arm of the patient during an interventional procedure. The flexible catheter 100 may be accessed through an introducer catheter via the radial artery incision. The flexible catheter 100 may be easily manipulated via a luer hub 101 while tracking through the vasculature to successfully engage the coronary artery. The flexible catheter 100 may serve as a guide and or delivery catheter for various therapeutic agents and devices.

In another aspect, a guidewire may be placed within the lumen of the flexible catheter system 100. The guidewire may be tracked through the catheter and through the radial artery located in the arm. The physician may track the invention through the brachial artery, and the flexible catheter system 100 may be tracked through the axially artery.

Figure 5:
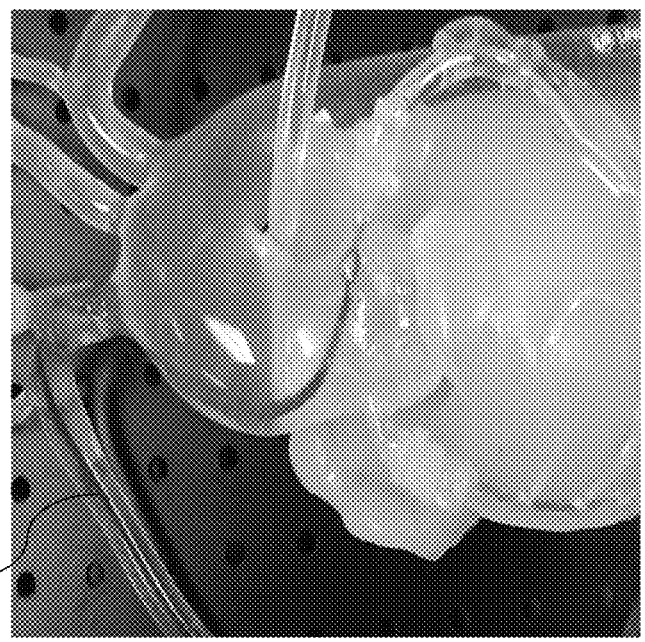
FIG. 5 depicts one embodiment of the flexible catheter system during a simulated procedure.

Now turning to FIG. 5, the flexible catheter system 100 is shown as it is being used during a simulated procedure. The catheter system 100 may be tracked through the right subclavian artery, and into the brachiocephalic trunk where the catheter may be positioned for access to its intended target in the ascending aorta. In one aspect, the flexible catheter system may be tracked through the ascending aorta, along the ascending aortic wall (not shown). While tracking near or along the ascending aortic wall, the catheter may be positioned for stability and backup force, which may be required for stable engagement of the Left Coronary Ostium.

Figure 6:
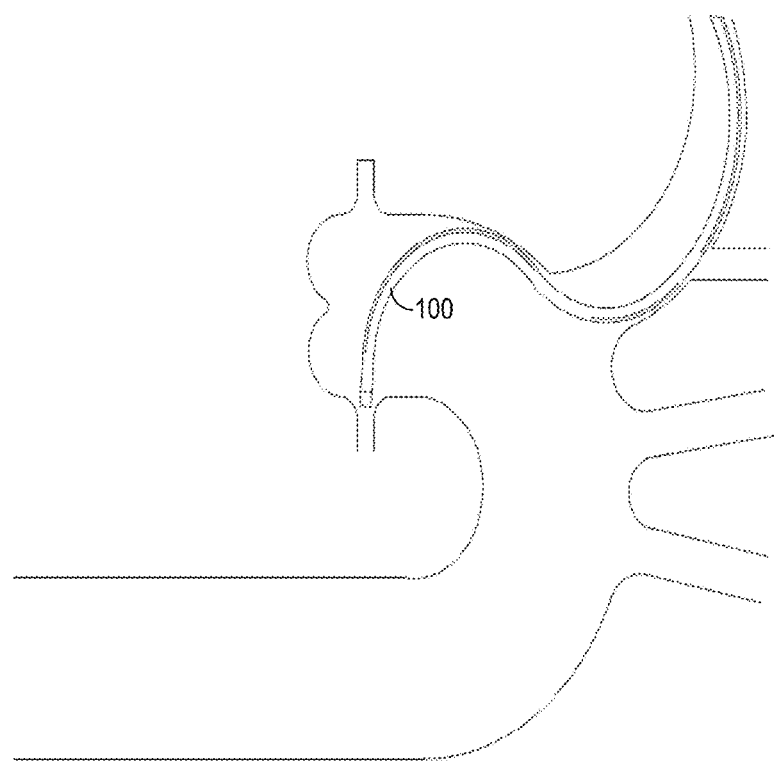
FIG. 6 depicts a schematic view of one embodiment of the flexible catheter system being used during a procedure.

FIG. 6 is a schematic view of one embodiment of the flexible catheter system being used during a procedure. The flexible catheter system 100 is depicted as being able to directly access the ostium due to its layered construction which enables the catheter to track with more control.

Some of the main advantages of the flexible catheter system may include: (1) The distal end of the catheter system may be introduced into the body via the artery of the arm to access the left coronary artery. Since the left coronary artery is characterized by having a maximum outer diameter throughout its body of 3 mm, the catheter outer diameter may range from 1 mm to 3 mm. (2) The catheter may be made and constructed using a blend of plastic based materials, stainless steel and Teflon to give it "shape memory" characteristics or to be able to maintain its shape. (3) The catheter may also be constructed with layers of the materials mentioned above which allow it to maintain its shape. (4) The catheter may have segmented curves in the flexible catheter body that enable it to maintain a shape required for tracking and engagement to the left coronary artery. (5) The segments of the catheter may be made of different grades and durometer of plastic based raw material. (6) The segments may allow the catheter to retain its shape memory in conjunction with the wire/fiber reinforcement. (7) When positioned to engage the left coronary artery, the catheter system may access and maintain back up via the contralateral wall of the ascending aorta. The catheter may also maintain back up via the lateral wall of the brachiocephalic artery. (8) The catheter may track near or against the ascending aorta wall creating a backup support and the backup force necessary for stable engagement of the Left Coronary Arteries. The backup force may be maintained via the lateral wall of the brachiocephalic artery. (9) The catheter may directly access the ostium due to its layered construction which enables the catheter to track with more control. (10) The catheter may traverse through variable tortuous vessels which are common in older and advanced aged populations. (11) The curved shape of the catheter may allow it to track through tortuous anatomy. When tracked and pushed through blood vessels, the "S" shape of the catheter may conform to the shape of the vessel unlike other radial catheters which are limited to traversing only one or two curves. (12) For example, the curves of the catheter may allow it to track through tortuous radial, tortuous brachial, tortuous axillary, tortuous right subclavian, tortuous brachiocephalic trunks and into the ascending aorta, conforming to the ascending aorta wall contralateral (opposite) to the target Left Coronary Artery ostium.

Numerous specific details are set forth to provide a thorough understanding of the present invention. However, those skilled in the art will appreciate that the present invention may be practiced without such specific details. In other instances, well-known elements have been illustrated in schematic or block diagram form in order not to obscure the present invention in unnecessary detail. Additionally, for the most part, specific details, and the like have been omitted inasmuch as such details are not considered necessary to obtain a complete understanding of the present invention, and are considered to be within the understanding of persons of ordinary skill in the relevant art.

Having thus described the present invention by reference to certain of its exemplary embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered desirable by those skilled in the art based upon a review of the foregoing description of exemplary embodiments. Accordingly, it is appropriate that any claims supported by this description be construed broadly and in a manner consistent with the scope of the invention.

What is claimed is:

1. A flexible catheter system, comprising:
a luer connector and a flexible catheter body, the flexible catheter body having a proximal end and a distal end, wherein the luer connector is connected to the proximal end of the flexible catheter body;
wherein the flexible catheter body, when in a relaxed state, comprises:
a proximal segment at the proximal end of the flexible catheter body, the proximal segment comprising a first end, a second end, and a substantially straight length, wherein the first end of the proximal segment is adjacent to the luer connector and the substantially straight length of the proximal segment extends to and comprises the second end;
a first curve segment extending directly from the second end of the proximal segment;
a body segment extending directly from the first curve segment in a direction substantially parallel and opposite to the direction of extension of the proximal segment;
a second curve segment extending toward the distal end of the catheter body in a curve opposite in a direction to the first curve segment; and
a distal segment at the distal end of the flexible catheter body, the distal segment comprising a substantially straight length extending directly from the second curve segment to a tip at the distal end of the catheter body in substantially the same direction and substantially parallel to the direction of extension of the proximal segment.

2. The catheter system in claim 1, wherein the flexible catheter body further comprises:
an inner layer with a lubricious path;
a middle layer as a reinforcing structure; and
an outer layer with shape memory characteristics.

3. The catheter system in claim 2, wherein the outer layer is coated with a hydrophilic or hydrophobic material.

4. The catheter system in claim 1, where in the flexible catheter body is coated with a hydrophilic or hydrophobic material.

5. The catheter system in claim 1, wherein the flexible catheter body comprises at least three or more layers.

6. The catheter system in claim 2, wherein the outer layer comprises a polyamide plastic mixture, blend or concentrate, a nylon mixed with a radiopaque filler, or a polyurethane mixed with the radiopaque filler, wherein the radiopaque filler is characterized by a mixture of barium, tungsten sulfate, bismuth trioxide and/or bismuth sub carbonate.

7. The catheter system in claim 2, wherein the middle layer comprises a wire coil or braid made of different grades of stainless steel, nylon fiber, or nitinol wire.

8. The catheter system in claim 2, wherein the inner layer is made of a polytetrafluoroethylene PTFE (Teflon), or a mixture of polytetrafluoroethylene (Teflon) and a plastic-based material that is lubricious when in use.

9. The catheter system in claim 1, wherein the proximal segment further comprises a length in the range from 810 to 820 mm.

10. The catheter system in claim 1, wherein the first curve segment further comprises a curve angle in the range of 30° to 210°.

11. The catheter system in claim 1, wherein the second curve segment further comprises a curve angle in the range of 70° to 250°.

12. The catheter system in claim 1, wherein the flexible catheter body has a catheter outer diameter that ranges from 1 mm to 3 mm.

13. The catheter system in claim 1, wherein the first and second curve segments enable the flexible catheter body to maintain a shape required for tracking and engagement to the left coronary artery.

14. The catheter system in claim 2, wherein the wire reinforcement of the middle layer helps the flexible catheter body to retain its shape memory.

15. The catheter system in claim 1, wherein the first and second curve segments each comprise a plastic-based material with varying soft to stiff durometer.

16. The catheter system in claim 1, wherein the distal segment further comprises a length in the range from 17 to 19 mm.

17. The catheter system in claim 1, wherein the first curve segment further comprises a curve radius in the range of 13 to 15 mm.

18. The catheter system in claim 1, wherein the second curve segment further comprises a curve radius in the range of 11 to 13 mm.

19. The catheter system in claim 10, wherein the first curve segment further comprises a curve angle in the range of 150° to 210°.

20. The catheter system in claim 19, wherein the first curve segment further comprises a curve angle of 165°.

21. The catheter system in claim 11, wherein the second curve segment further comprises a curve angle in the range of 130° to 250°.

22. The catheter system in claim 21, wherein the second curve segment further comprises a curve angle of 180°.

23. The catheter system in claim 1, wherein the flexible catheter body is configured such that, when the flexible catheter body is introduced through an artery in the arm and tracked against the ascending aortic wall for engagement of the left coronary ostium, the substantially straight length of the distal segment is substantially coaxially aligned with the ostium of the left coronary artery.

24. The catheter system in claim 1, wherein the flexible catheter body is configured such that, when the flexible catheter body is seated in the ascending aortic wall, the second curve segment provides backup support and applies backup forces to the flexible catheter system.

25. The catheter system in claim 1, wherein the sum of the curve angles of the first curve segment and the second curve segment is zero.

26. The catheter system in claim 1, wherein the curve angle of the first curve segment and the curve angle of the second curve segment are substantially equivalent.

27. The catheter system in claim 1, wherein the distal segment is spaced laterally from the proximal segment.

28. The catheter system in claim 1, wherein the first curve segment and the second curve segment comprise an "S" shape configuration of the catheter body between the proximal segment and the distal segment.

29. The catheter system in claim 1, wherein the entire length of the proximal segment is substantially straight between the luer connector and the first curve segment.

30. The catheter system in claim 1, wherein the proximal segment is immediately adjacent to the luer connector.

31. A flexible catheter system, comprising:
a luer connector and a flexible catheter body, the flexible catheter body having a proximal end and a distal end, wherein the luer connector is connected to the proximal end of the flexible catheter body;
wherein the flexible catheter body, when in a relaxed state, comprises:
a substantially straight proximal segment at the proximal end of the flexible catheter body, the proximal segment having a first end and a second end, wherein the first end of the proximal segment is adjacent to the luer connector, and the second end of the proximal segment extends directly into a first curve segment;
wherein the first curve segment further comprises a curve angle in the range of 150° to 210°;
a body segment extending directly from the first curve segment in a direction substantially parallel to the proximal segment;
a second curve segment;
a substantially straight distal segment at the distal end of the flexible catheter body, wherein the distal segment extends directly from the second curve segment; and
wherein the second curve segment comprises a curve angle in the range of 130° to 250° and wherein the distal segment extends from the second curve segment in a direction opposite to a portion of the flexible catheter body extending between the first curve segment and the second curve segment.

32. A flexible catheter system, comprising:
a luer connector and a flexible catheter body, the flexible catheter body having a proximal end, wherein the luer connector is connected to the proximal end of the flexible catheter body;
wherein the flexible catheter body, when in a relaxed state, comprises:
a proximal segment at the proximal end of the flexible catheter body, the proximal segment comprising a substantially straight length;
a first segment extending directly from the proximal segment and extending through an angle of curvature in a first direction of curvature;
a body segment extending directly from the first curve segment in a direction substantially parallel and opposite to the direction of extension of the proximal segment;
a second segment between the proximal segment and the distal end and extending through an angle of curvature in a second direction opposite the angle of curvature of the first segment; and
a distal segment comprising a substantially straight length and comprising a tip of the catheter body, wherein the distal segment is disposed laterally from the proximal segment and extends both substantially parallel to and in substantially the same direction of extension along the catheter body as the proximal segment.

* * * * *